United States Patent [19]

Barsan

[11] Patent Number: 4,631,294

[45] Date of Patent: Dec. 23, 1986

[54] TREATMENT OF CEREBRAL ISCHEMIA WITH DICHLOROACETATE

[75] Inventor: William G. Barsan, Cincinnati, Ohio

[73] Assignee: University E.M., Inc., Cincinnati, Ohio

[21] Appl. No.: 752,091

[22] Filed: Jul. 5, 1985

[51] Int. Cl.$^4$ ............................................. A61K 31/19
[52] U.S. Cl. .................................................... 514/557
[58] Field of Search ....................................... 514/557

[56] References Cited

U.S. PATENT DOCUMENTS 3,179,562  4/1965  Hoffman ................................. 167/5
4,122,188 10/1978  Stacpoole ............................. 424/317

OTHER PUBLICATIONS

Treatment of Lactic Acidosis with Dichloroacetate in Dogs; *The Journal of Clinical Investigation;* vol. 70; Oct. 1982; pp. 853–862.
Effects of Dichloroacetate on Brain Tissue Pyruvate Dehydrogenase; *Journal of Neurochemistry;* vol. 41, Nov. 4, 1983; pp. 1052–1056.
Effects of Dichloroacetate on Brain Pyruvate Dehydrogenase; *Journal of Neurochemistry;* vol. 42; Nov. 1, 1984; pp. 38–42.
Metabolic Effects and Pharmacokinetics of Intravenously Administered Dichloroaetate in Humans; *Diabetologia;* Spring 1980; pp. 109–113.
The Metobolic Effects of Dichloroacetate; Metabolism; vol. 30, No. 10, Oct. 1981; pp. 1024–1039.
Dichloroacetate Tissue Concentrations and Its Relationship to Hypolactatemia and Pyruvate Dehydrogenase Activation; *Biochemical Pharmacology;* vol. 31, Nov. 19, 1982; pp. 3124–3126.
Metabolic Effects of Dichloroacetate in Patients with Diabetes Mellitus and Hyperlipoproteinemia; *New England Journal of Medicine;* Mar. 9, 1978; pp. 526–530.
Toxicity of Chronic Dichloroacetate; *New England Journal of Medicine;* Feb. 15, 1979; p. 372.
Metabolic Effects of Sodium Dichloroacetate in Normal and Diabetic Dogs; Diabetes; vol. 28, Sep. 1979; pp. 852–857.
Biological Disposition of Sodium Dichloroacetate in Animals and Humans after Intravenous Administration; *The Journal of Pharmaceutical Sciences;* Apr. 1980; pp. 419–421.
Treatment of Lactic Acidosis with Dichloroacetate; *New England Journal of Medicine;* Aug, 18, 1983; vol. 309, No. 7; pp. 390–396.

*Primary Examiner*—Stanley J. Friedman
*Attorney, Agent, or Firm*—Charles R. Wilson

[57] ABSTRACT

A method of treating a victim suffering from cerebral ischemia or treating a patient expected to suffer an ischemic insult comprises administering a therapeutically effective amount of a dichloroacetate. The post-treatment occurs within about 48 hours of the ischemic insult and lasts for up to about two days.

18 Claims, No Drawings

TREATMENT OF CEREBRAL ISCHEMIA WITH DICHLOROACETATE

This invention relates to a method of treating victims of cerebral ischemia. More particularly, this invention relates to a post-treatment of cerebral ischemia victims or a pre-treatment of a patient likely to suffer cerebral ischemia using an effective amount of a dichloroacetate.

BACKGROUND OF INVENTION

Cerebral ischemic insult is one of the most clinically significant conditions leading to irreversible brain cell damage and death. Causes of cerebral ischemia include shock, cardiac arrest, head trauma and stroke. All of the aforementioned medical conditions result in an interruption or significant decrease in the flow of blood to parts of the brain. The continued flow of blood, as a life sustaining source of oxygen and glucose, is necessary to maintain normal brain function. Any time the flow of blood to the brain is interrupted for any length of time there is the danger that ischemic brain cell damage will occur.

Of all the causes of cerebral ischemia the one of greatest concern, because of its relative high incidence of occurrence, is stroke. Ischemic stroke may be due to many causes, though the main cause is atherosclerosis. Atherosclerosis results in the inside circumference of an artery gradually becoming smaller, thereby restricting the flow of blood. Formation of a clot in an artery leading to the brain or migration of a blood clot from other areas is another cause which obstructs the flow of blood.

It had been thought that an interruption in the flow of blood to a specific area of the brain would cause permanent brain damage if not corrected within minutes. For those victims who had not received any warning signs, a stroke or other cerebrovascular insult with its resultant damaging effects could not be prevented. That is, permanent brain damage with a consequent loss of physical and mental function was viewed as unavoidable following a stroke. It was primarily because of this belief that most efforts connected with a study of stroke centered on how to prevent a stroke from occurring and how to rehabilitate a stroke victim through physical therapy. Very little research is known which has as its object the early treatment of a stroke victim to prevent or at least alleviate brain damage early in the course of a stroke.

There is a definite need for a treatment to prevent brain damage in ischemic insult victims. Necessarily, such a treatment would have to be effective shortly after administration before irreversible damage occurred. Additionally, there is a need to pre-treat a patient who has an increased chance of suffering a stroke in the near future. For example, a known possible consequence of surgery on the carotid artery to remove plaque formation is that a stroke may occur. A pretreatment of the patient prior to surgery which would alleviate or eliminate any brain damage from a subsequent stroke would be desired.

There has now been discovered a method whereby a victim or possible victim of a stroke or other cause of cerebral ischemia can be treated to prevent the occurrence of permanent brain damage. This treatment of the victim has been found to safely and effectively alleviate the debilitating effects of brain cell damage.

SUMMARY OF INVENTION

This invention relates to a method of alleviating damage caused by cerebral ischemia in a mammal comprising treating said mammal with a therapeutically effective amount of a composition containing as its active substance a pharmaceutically acceptable salt of dichloroacetic acid, e.g. sodium dichloroacetate. The active substance is either administered to a victim within about 48 hour of his first suffering an ischemic insult or is administered to a patient who is likely to suffer cerebral ischemia in the immediate future. In either case, the likelihood of permanent brain damage is substantially reduced.

DETAILED DESCRIPTION OF THE INVENTION

According to this invention, the post-treatment of cerebral ischemia victims or the pre-treatment of possible cerebral ischemia victims is accomplished by administering a therapeutically effective amount of a dichloroacetate. Described in more detail below are the specific active substances, how formed into pharmaceutical compositions and specific methods of treatment. The active substance used in the method of this invention is a pharmaceutically acceptable salt of dichloroacetic acid.

Salts of dichloroacetic acid are well known and commercially available. Specific pharmaceutical salts include those formed by the alkali metal and alkaline earth metal ions such as sodium, potassium, calcium, and magnesium, ammonium, and substituted ammonium where the substituent is a mono- or di-lower alkyl radical of 1-4 carbon atoms and ethylene di-ammonium. Specific pharmaceutical salts useful in this invention include sodium dichloroacetate, potassium dichloroacetate, and diisoproyl ammonium dichloroacetate. The sodium dichloroacetate is highly preferred.

The dichloroacetate is formulated into a composition suitable for administering to a mammal. Preferably, the composition is administered parenterally so as to accelerate its travel to the brain cells requiring the treatment. As discussed below, time is quite important, it being found that the longer cells are ischemic, the higher the likelihood that there will be permanent neurologic deficits. In stroke, it is known that progression or extension of neurologic deficits may occur within the first 24 to 48 hours after the onset of stroke. Therefore, it would be important that any treatment should be started within about 48 hours after the onset of neurologic deficits. While the preferred method of administering the active substance is intravenously, it can also be administered perorally in the form of pills, tablets, capsules (encapsulated by gelatin or some other dissolvable material), syrup, liquid, suspension or emulsion.

The compositions contain the dichloroacetate as the active substance and appropriate pharmaceutically acceptable carriers, diluents and adjuvants. The amount of dichloroacetate in the composition will vary widely from about 0.5% to 99.5% by weight of the total composition depending primarily on the mode of administration. The pharmaceutical carrier selected and any other optional component is based on the chosen route of administration in accord with standard pharmaceutical practice.

Examples of pharmaceutical carriers used when a parenteral solution is formulated include water and oils. Oils included are those of petroleum, animal, vegetable or synthetic origin such as peanut oil, soybean oil, mineral oil and sesame oil. Glucose and related sugar solutions and glycols such as propylene glycol and polyethylene glycol are also examples of such pharmaceutical carriers. Water is the preferred carrier when the composition is administered intravenously. Aqueous dextrose and glycol solutions are preferred carriers when the composition is administered by injection.

Examples of pharmaceutical carriers used when the composition is administered perorally include starch, glucose, lactose, sucrose, gelatin, silica gel, magnesium stearate, water, and ethanol. "Remington's Pharmaceutical Sciences," by E. W. Martin contains other examples of well known and acceptable carriers.

With reference to the treatment of victims who have suffered cerebral ischemia, it has been found the method of this invention is significantly more effective when used on a victim within about 48 hours of his first suffering an ischemic insult. Preferably, the dichloroacetate is administered within about 12 hours and more preferably within about 60 minutes of the victim first suffering the ischemic insult. The treatment is episodic in that the victim is periodically treated for up to about two days. If no progress is noticed after this limited treatment, further dosages of the dichloroacetate is stopped. Preferably, from about 12.5 milligrams per kilogram (weight of victim) to about 300 milligrams per kilogram, more preferably about 25 milligrams per kilogram to about 50 milligrams per kilogram of the dichloroacetate is administered per dose for up to two days. The required dosage is preferably administered at least three times per day, more preferably from three to six times per day over the two days. The exact dosage level and time span over which the dichloroacetate is administered will depend on the size and age of the mammal (specifically humans), his state of health, degree of suspected brain cell damage and tolerance to any adverse side effects of the dichloroacetate.

The method of this invention is also useful for pretreating possible victims of cerebral ischemia. If an event such as certain types of surgery on a patient is about to occur, the patient is given an effective dosage level of the dichloroacetates of this invention. Preferably, dosage levels of about 12.5 milligrams per kilogram to about 300 milligrams per kilogram, more preferably about 25 milligrams per kilogram to about 50 milligrams per kilogram of the dichloroacetate is administered to a patient prior to the event which could cause cerebral ischemia. The patient who subsequently suffers a stroke or some other ischemic insult will not experience the same extent of brain cell damage as occurs without the dichloroacetate pretreatment.

It is theorized that when cerebral ischemia occurs, there is an accelerated formation of lactic acid in the affected brain cells. This occurs whether the ischemia is caused by a stroke, cardiac arrest or head trauma. The presence of the lactic acid lowers the intracellular pH which in turn interferes with normal cell structure and function. The net result is cellular death. It has been found that the debilitating effects of severe ischemia may not become permanent until at least 60 minutes have passed. Thus, the timely administering of the dichloroacetate described above will effectively reduce the initial lactic acidosis and prevent extensive and irreversible brain cell damage. The fact that sufficient time is available before irreversible brain cell damage occurs and the effectiveness of limited dosages of the dichloroacetates of this invention are surprising.

The following examples illustrate this invention.

Example I

Numerous animal studies have shown that brain tissue accumulates lactic acid in large quantities when cerebral ischemia occurs. It is further known that the higher the brain tissue lactic acid level, the smaller the chance of a normal neurologic outcome. This example illustrates how brain lactate levels are reduced by the use of sodium dichloroacetate.

Fasted male Wistar rats are used in the study. Twelve of the rats are used as a control with six being given 0.5 milliliters (ml) water intravenously and six being given 25 milligrams/kilogram weight (mg/kg) sodium dichloroacetate (DCA) in 0.5 ml water intravenously, prior to being tested for brain lactate levels. Twenty-one of the rats are subjected to 30 minutes of partial global ischemia (PGI) by a combination of bilateral carotid ligation and hypotension in the manner described by Rehncrona S., Rosen I. and Siesjo Bk, J. Cerel Blood Flow Metabol 1:297-311, (1981). Of the twenty-one rats subjected to the PGI, six receive 0.5 ml of water intravenously prior to the PGI, six receive 25 mg/kg DCA in 0.5 ml water intravenously prior to the PGI, four receive 25 mg/kg DCA in water intravenously after 30 minutes of the PGI and five receive 25 mg/kg DCA in 0.5 ml water intravenously after 45 minutes of the PGI. Results of the tests are as follows:

| Experimental Group | Number of Animals | Brain Lactate (u M/g) |
|---|---|---|
| Control with pre-ischemic vehicle | 6 | 3.12 |
| Control with pre-ischemic DCA treatment | 6 | 3.19 |
| Ischemic with pre-ischemic vehicle | 6 | 9.85 |
| Ischemic with pre-ischemic DCA treatment | 6 | 3.29 |
| Ischemic with post-ischemic DCA treatment (30 minutes) | 4 | 3.20 |
| Ischemic with post-ischemic DCA treatment (45 minutes) | 5 | 5.65 |

The above results show that treatment of a mammal with a dichloroacetate either prior to or immediately after an ischemic insult keeps the level of brain lactate from rising significantly above what is found in the controls. The increase of brain lactate level in the rats subjected to PGI without treatment with the dichloroacetate is significant.

The following examples illustrate various forms in which the active substance can be formulated.

EXAMPLE II

A composition formulated for intravenous administration is as follows:

| Sodium dichloroacetate | 50 parts by weight |
|---|---|
| Water | 1000 parts by weight |

EXAMPLE III

Gelatin capsules contain the following components:

| Sodium dichloroacetate | 250 milligrams |
|---|---|

| | |
|---|---|
| Lactose filler | 250 milligrams |

EXAMPLE IV

A liquid syrup for oral administration contains:

| | |
|---|---|
| Sodium dichloroacetate | 500 milligrams |
| Raspberry acacia syrup | 1000 milligrams |

What is claimed is:

1. A method of alleviating brain damage caused by cerebral ischemia in a mammal comprising parenterally administering thereto a therapeutically effective amount of a composition containing as its active substance a pharmaceutically acceptable salt of dichloroacetic acid.

2. The method of claim 1 wherein the composition is administered for up to about two days.

3. The method of claim 1 wherein at least three doses per day of from about 12.5 milligrams per kilogram to about 300 milligrams per kilogram of the dichloroacetate per dose for up to two days is administered.

4. The method of claim 3 wherein at least three doses per day of from about 25 milligrams per kilogram to about 50 milligrams per kilogram of the dichloroacetate per dose for up to two days is administered.

5. The method of claim 3 wherein the active substance is sodium dichloroacetate.

6. The method of claim 1 wherein the composition is administered intravenously.

7. The method of claim 1 wherein the dichloroacetate is administered after an ischemic insult.

8. The method of claim 7 wherein the composition is administered within 48 hours of the occurrence of an ischemic insult.

9. The method of claim 8 wherein the composition is administered within 12 hours of the occurrence of an ischemic insult.

10. The method of claim 9 wherein the composition is administered within 60 minutes of the occurrence of an ischemic insult.

11. The method of claim 1 wherein the dichloroacetate is administered before an event which may lead to ischemic insult.

12. The method of claim 1 wherein the mammal is a human being.

13. The method of claim 1 wherein the cerebral ischemia is caused by a stroke.

14. The method of claim 1 wherein the cerebral ischemia is caused by increased intracranial pressure associated with head trauma.

15. The method of claim 1 wherein the cerebral ischemia is caused by direct brain damage from head trauma.

16. The method of claim 1 wherein the cerebral ischemia is caused by cardiac arrest.

17. The method of claim 1 wherein the pharmaceutically acceptable salt of the dichloroacetic acid is in the form of an alkali metal, alkaline earth metal, ammonium, substituted ammonium where the substituent is a mono- or di-lower alkyl radical of 1-4 carbon atoms or ethylene di-ammonium salt.

18. The method of claim 17 where the active substance is sodium dichloroacetate, potassium dichloroacetate or diisopropyl ammonium dichloroacetate.

* * * * *